United States Patent [19]

Damato

[11] Patent Number: 4,995,717

[45] Date of Patent: Feb. 26, 1991

[54] DEVICE FOR MOVING EYE CAMPIMETRY

[75] Inventor: Bertil E. Damato, Glasgow, Scotland

[73] Assignee: The University Court of the University of Glasgow, Glasgow, Scotland

[21] Appl. No.: 397,139

[22] Filed: Aug. 22, 1989

[51] Int. Cl.⁵ .............................................. A61B 3/02
[52] U.S. Cl. ..................................... 351/224; 351/239
[58] Field of Search ................ 351/224, 237, 239, 243

[56] References Cited

U.S. PATENT DOCUMENTS

| | | | |
|---|---|---|---|
| 3,827,789 | 8/1974 | Molner et al. | 351/237 |
| 4,059,348 | 11/1977 | Jernigan | 351/237 |
| 4,349,250 | 9/1982 | Gelius | 351/239 |
| 4,421,392 | 12/1983 | Pitts Crick et al. | 351/239 |
| 4,634,243 | 1/1987 | Massof et al. | 351/224 |

Primary Examiner—Rodney B. Bovernick
Assistant Examiner—J. P. Ryan
Attorney, Agent, or Firm—Krass & Young

[57] ABSTRACT

The computer-assisted moving eye campimetric device is a computer display of a moveable test grid having a central reference spot. The patient's eye is kept focussed on the spot by giving the patient the task of keeping the moving spot in a circle by operating a hand held mouse. With the patient's eye correctly focussed on the reference spot, target elements in the field of vision are successively illuminated and the patient reacts by pressing a button on the mouse. Failure to react indicates impaired vision at that point in the patient's visual field. The results are held in the computer memory and plotted out as a map of the patient's effective field of vision.

9 Claims, 2 Drawing Sheets

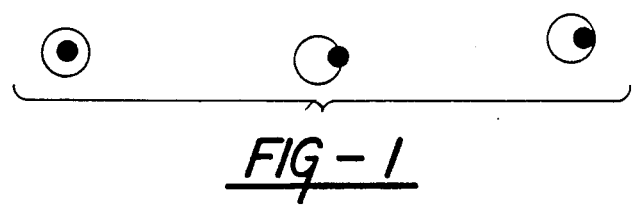
FIG-1
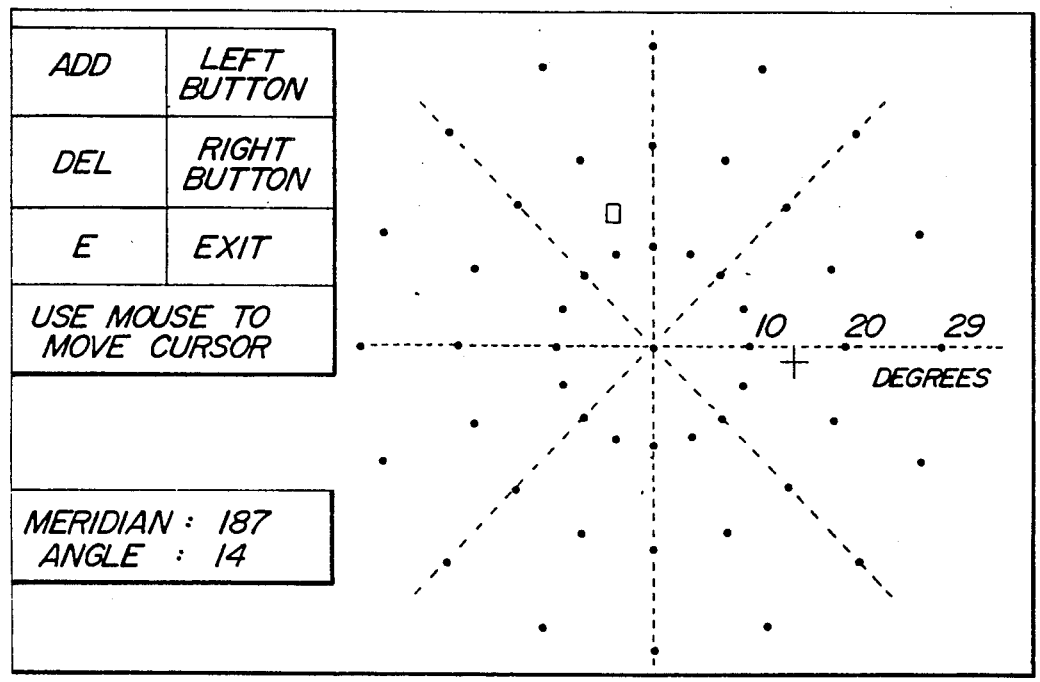
FIG-2
FIG-3
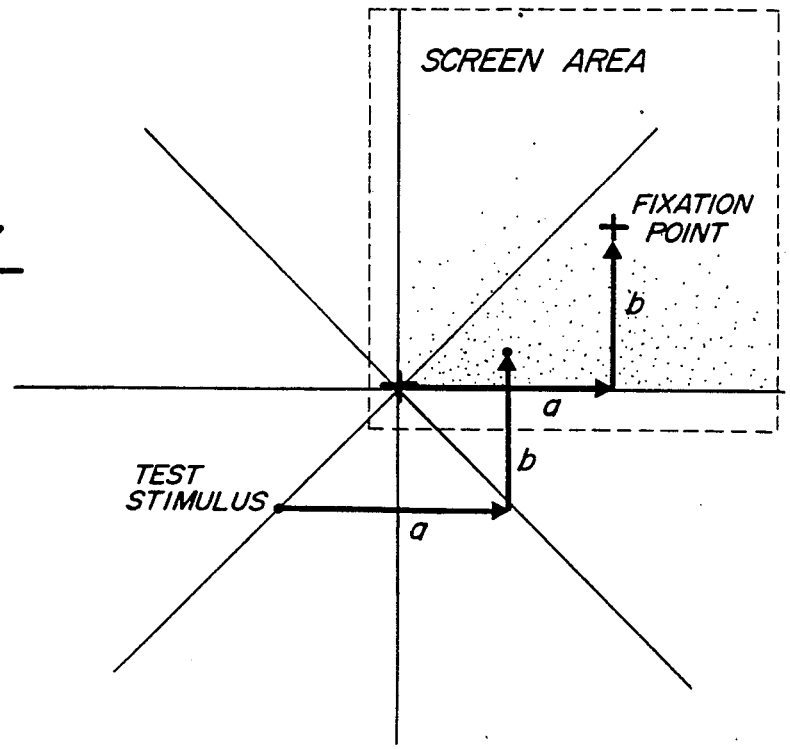

4,995,717

DEVICE FOR MOVING EYE CAMPIMETRY

FIELD OF THE INVENTION

The invention relates to a device for measuring a patient's effective field of vision, so as to identify any abnormal "blind spots" where vision is impaired.

BACKGROUND OF THE INVENTION

Several disorders of the eye and brain can cause extensive loss of peripheral vision before affecting the central vision. These include conditions such as glaucoma, cerebrovascular disease and pituitary tumours (Harrington, 1981). The measurement of the distribution and depth of peripheral visual defects is very useful in the diagnosis and management of such conditions (Keltner et al, 1983).

Perimetry has long been established as a useful method of recording visual function, measuring light sensitivity throughout a defined portion of the visual field and determining the position and extent of all areas of reduced visual perception (Harrington et al, 1981). The normal monocular visual field extends to over 100 degrees, but it is often sufficient to test only the central 30 degrees (Schulzer et al, 1987, Weber et al, 1986). In conventional methods of perimetry the subject's eye is fixed on a central stationary target while stimuli are presented at predetermined points in the visual field. However, there is a natural tendency for individuals to look away from the fixation point towards the test stimulus in an attempt to improve the test result. A skilled examiner and/or expensive equipment with considerable co-operation from the patient are all required to ensure that the eye remains immobile throughout the test. Despite these measures, many patients, particularly young children, the elderly and those with neurological deficits, are unable to keep the eye still for long enough and the test has to be abandoned. Failure may also result from loss of interest due to the repetitive nature of the test. Our previous U.S. Pat. No. 4737024 discloses such an oculo-perimetric method and device.

Many automatic visual field tests have been described previously, some using computer graphics (Accornero et al, 1984; Frisen et al, 1986) and other specifically designed for use in children (Fausset et al, 1986). However, none have addressed themselves successfully to the problem of maintaining both fixation and interest whilst keeping the test procedure simple and the equipment inexpensive.

In an effort to mitigate these problems, a method has been developed which allows the subject's eye to move during the procedure and uses the guise of a game to maintain interest.

SUMMARY OF THE INVENTION

The present invention provides an oculoperimetric device for use in measuring the field of vision of a patient, which comprises an extended area visual target having a plurality of discrete localised target elements disposed adjacent a reference target element at a plurality of different angular and radial positions relative to the reference target;

means for moving the visual target in a two-dimensional plane so as to keep the patient's attention fixed on the moving reference target element;

follower means movable by the patient to follow the movement of the reference target element;

the localised target elements being visible or invisible to the patient, and each target element appearing visibly at least once during a test sequence;

monitoring means operable by the patient dependent on whether or not he sees the appearance of each individual target element as it becomes visible; and recording means for recording whether or not each target element is seen by the patient, such as to provide a map of the patient's effective field of vision.

In a preferred embodiment of the invention, the device is in the form of a computer and the extended area visual target is moved around a computer screen in an apparently random manner. The reference target is constantly or intermittently visible to the patient, who has to track it around the screen using the follower means. Thus, the patient's attention is always focussed on the reference target as he attempts to follow it around the screen. The reference target is usually a bright spot (or could be a black spot on a light background), and the follower means is a circle which the patient moves around the screen in pursuit of the spot by means of a computer mouse. The object is to keep the spot inside the circle. If the spot goes outside the circle, the test is interrupted until the circle is once again brought around the spot. However, the sole purpose of the exercise is to keep the patient's eye focussed on the spot.

Alternatively, the invention could be embodied in a physically movable test grid which is moved in front of the patient's eye as the individual target elements are illuminated.

Embodiments of the invention will now be described by way of example only.

BRIEF DESCRIPTION OF THE DRAWINGS

FIG. 1 shows the central reference target (spot) and the follower means (circle) in three positions inside, not-inside, and touching;

FIG. 2 is a representation of the computer screen display showing the placement of the target elements on the visual target test grid;

FIG. 3 shows the manner in which the test grid is moved around the screen so as to keep the patient's eye focussed on the central reference spot, the test grid being about four times the size of the screen;

DETAILED DESCRIPTION OF PREFERRED EMBODIMENTS

Figure 4:
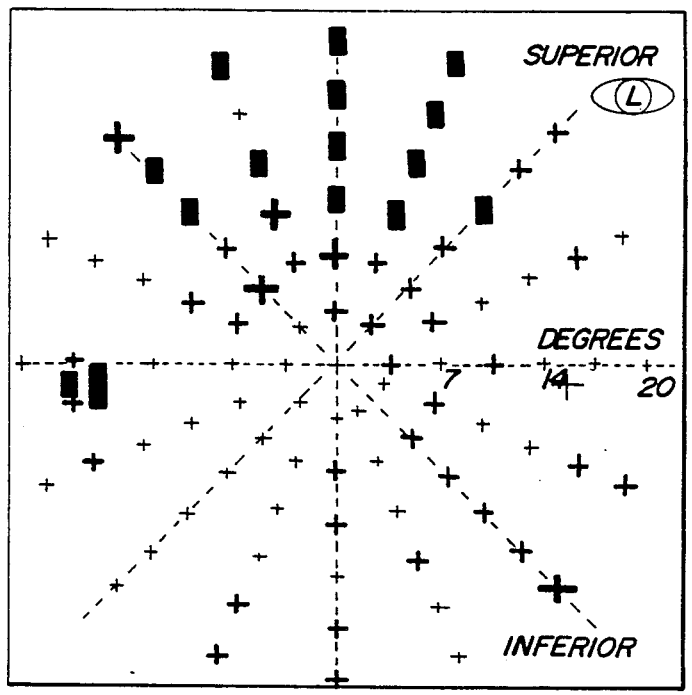
FIG. 4 shows a plot of the left visual field of a 60 year old man showing a superior defect and the normal blind spot.

The test has been designed on an IBM AT Personal Computer with Enhanced Graphics Display (EGA) and the software written in BASIC. It is implemented with the subject's eye at a fixed distance from the computer screen and it is possible to test the central 30 degrees using a 12 inch monitor with a user to screen distance of 24 cms. The background and foreground colours for the test can be selected from a palette of 10 shades.

(1) Fixation Method and Stimulus

An entirely new method is used to hold fixation. Unlike previous tests in which a subject's eye is fixed on a central stationary target, the test does not require an immobile eye.

The fixation point essentially consists of a spot whose radius can be varied from 1 to 8 pixels. At its minimum value it subtends 1.3 degrees and at its maximum, 1.9 degrees, useful in patients with poor visual acuity.

The fixation stimulus is initially surrounded by a circle whose movement the subject is able to control using the computer's mouse. The fixation spot oscillates in a horizontal direction across the screen and must be maintained inside the circle for the presentation of test stimuli to proceed (FIG. 1). If the spot touches the circle, an unpleasant noise is emitted by the computer and the appearance of the test stimulus is delayed. The ease with which this task can be accomplished can be altered by varying the speed of movement of the spot (5 possible speeds) or its size relative to the circle. These conditions can be altered either automatically by the computer or manually in a preliminary test immediately prior to the examination. If necessary the size of both the spot and the circle can be increased to accommodate patients with poor central vision. In this way fixation is maintained at a satisfactory level.

Typically, the spot oscillates for about 5 seconds during which time a test stimulus appears. The stimulus is visible for a preset time. Then the spot disappears for a time interval and reappears at another randomly selected position on the screen, where it oscillates again.

Test Stimulus

The sensitivity of the test can be set by selecting one of eight stimuli which are solid circles effectively subtending from 0.1 to 1.2 degrees. The size of the circle can also be varied.

While the subject's eye is focussed on the fixation target, test stimuli are silently presented on the computer screen in predetermined positions in a random order. The subject signals awareness of their presence by pressing a button on the mouse, a rewarding sound is emitted and the stimulus is recorded as seen. If the subject fails to respond in a preset time interval the stimulus silently disappears and is recorded as missed.

If the button is pressed when no stimulus is present this is judged to be a fixation loss and the appearance of the next stimulus is delayed until fixation is deemed to be satisfactory these illegal responses also signalled by annoying beeps and recorded as a measure of patient reliability.

The duration of the stimulus presentation and the time between successive presentations can be specified prior to examination. If these are then found to be unsuitable they can easily be altered and the test restarted.

The stimulus should appear at a time after the reappearance of the fixations spot which exceed the time which the oscillating spot would take to leave, the circle, if the patient leaves the circle unmoved. This ensures that the patient's fixation on the spot is being maintained. For an average patient the time is usually from 0.5 to 2.0 seconds. A longer time of from 1.5 to 3.0 seconds may be more appropriate for a patient of impaired vision, since he is likely to take longer to find the fixation spot. The test is interrupted if the patient sees the stimulus first, without having seen the fixation spot.

Missed stimuli can be retested at the same size to verify their non-visualisation or retested at a larger size to assess the depth of a defect.

The procedure is repeated until all stimuli have been presented and the results can be save to disk, plotted, or viewed on the screen.

(3) The Test Grid

The location of test points in the visual field are chosen by defining an array of points, known as the test grid (FIG. 2). The program offers a choice of four basic test grids which can be modified to suit individual patient requirements. The most complex of these consists of 96 points arranged in polar formation, with radius r, ranging from 2.3 cm to 13.9 cm and meridian, theta, from 0 to 360 degrees in 22.5 degree intervals. The grid therefore subtends the central 30 degrees with points situated approximately every 4.7 degrees, when viewed at a distance of 24 cms. Points can easily be added to or deleted from this grid using a cursor, with a maximum of 100 points. Points are added by pressing the ADD and deleted by using DEL. The degree of eccentricity and the meridian of the cursor position within the grid are displayed in order to facilitate precise positioning of test stimuli in the visual field.

For each test point four test attributes can be set: size, colour, duration of presentation, and delay before presentation. The fixation point is located at the centre of the grid and similarly its size, colour and duration before stimulus presentation can be set. An area effectively four times the size of the computer screen is used, with fixation point and test stimulus being moved into the screen area by a suitable offset. (FIG. 3)

(4) Presentation of Test Results the test results are plotted on a scaled down version of the test grid with patient details, test attributes and numerical test results plotted beneath (FIG. 4). Points seen on their first presentation are displayed as small horizontal lines, whilst those seen on successive presentations are shown as increasingly larger and thicker crosses. Points not seen on the final presentation are shown as solid squares. The results can be viewed on the screen and a hardcopy obtained if necessary.

From the resulting visual field pattern the ophthalmologist is able to recognise any abnormality.

(5) Program Operation

The program is menu driven and requires a password for access. The appropriate test screen is set from the specified machine parameters—namely graphics standard and screen dimensions and the user is then presented with the following menu:
Enter patient details
Select a default test
Retrieve an alternative test from disk
Design a new test
Change test attributes
Calibrate screen luminance levels
Start the test procedure
View, plot, or save the test results Exit.

Individual test parameters from a previously selected test may be altered without executing the entire test selection procedure and the modified test saved to disk. A demonstration of the test may be given to the patient and a training period is allowed for familiarisation with test equipment and method. At this stage the difficulty of the test can be tailored to suit the individual patient with the relevant parameters altered either automatically or manually.

The test can be paused, restarted or aborted at any time without losing partial results. The response or absence of response to each test stimulus is recorded with the size of the stimulus presented. Patient progress can also be viewed at any time during the test.

(6) Hardware

The test has been developed for use on the IBM Personal Computer and exact compatibles. A 12 inch monitor with Enhanced Colour Display and EGA graphics card are required for high resolution colour graphics; however the test will support CGA standard graphics and a monochrome monitor with subsequent reduced resolution and range of colour. A Microsoft mouse is used for optimum patient interaction, but keyboard and joystick versions of the test would be possible. An Epson compatible printer provides a hardcopy of the test results.

Standard screen luminance levels can be set prior to the examination using a photometer. A headrest assembly ensures that patient's eye remains at a fixed distance from the computer screen throughout the test.

(7) Results

Figure 5:
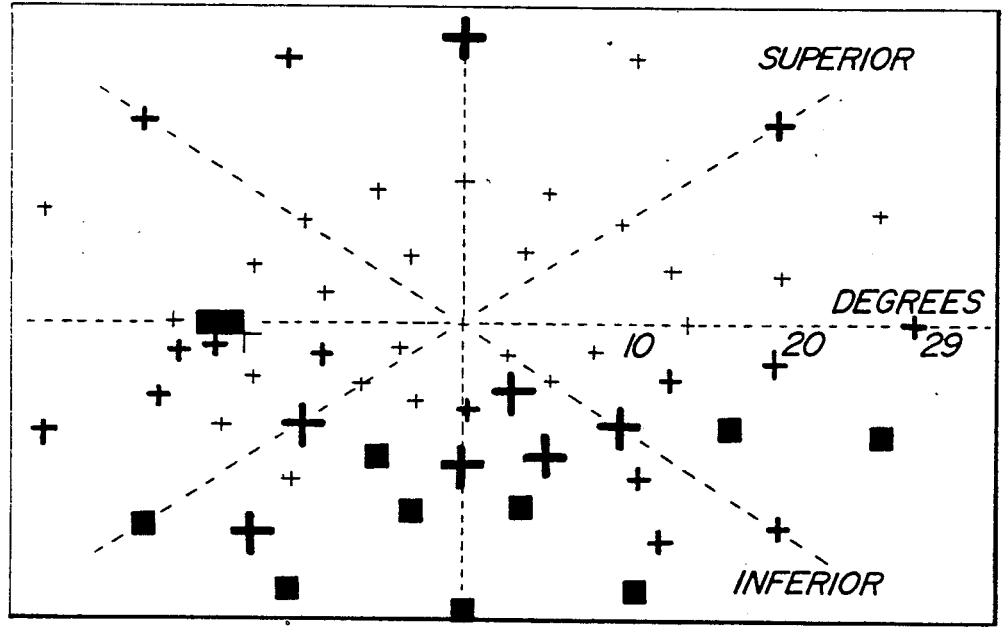
FIG. 5 shows a plot of an inferior arcuate defect with a nasal step and slight superior constriction in a 43 year old woman with glaucoma.

In spite of the fact that this test uses an entirely new method to test the visual field, it furnishes very similar results to conventional methods (FIG. 5). In the examination of 16 eyes in 10 normal volunteers, the blind spot was accurately and reproducibly located at 15 degrees in all cases and the average testing time was 3.2 $\pm/-1.2$. (SD) mins. The time taken to perform visual field examination is very dependent on the number of stimuli tested, patient dexterity and patient co-operation. All individuals tested had normal visual fields and were tested using 26, 0.1 degree stimuli.

Using the format of a game helps to maintain a child's interest and consequently improves fixation. The story of the game can be adapted to suit each individual child, but essentially, subjects are instructed that the spot inside the circle must not be allowed to escape and if the see any "other subjects" on the screen coming to rescue it, these can be captured by pressing a button on the mouse.

Children who have been tested have enjoyed the game-like aspects of the procedure and have had no difficulty in maintaining their interest for its duration. Their fixation was also good, with no real opportunity for their eye to wander due to the design of the test.

Because the accuracy of the test is so dependent on the co-ordination of the patient, a short demonstration/-training program has been developed to be executed prior to the examination, enabling the user to finely tailor the level of difficulty of the test to suit the individual patient.

The speed of the fixation target is important. If it moves too slowly then the patient finds the test procedure simple and his attention starts to wander. This can result in a loss of fixation. Conversely, if the fixation target moves too quickly then the patient may not be able to keep the circle over it and he quickly loses interest, again resulting in a loss of fixation. During the demonstration period, the computer monitor's the patient's success at keeping the circle over the fixation target, increasing the fixation speed if the test appears too easy and decreasing it if it appears too difficult. The level of difficulty of the test can further be altered by changing the size of the circle. These parameters do not make the test more difficult visually, but rather increase its concentration requirements and maintain fixation at a satisfactory level.

Although the test has been developed for use primarily in children, it could also be useful in adults and is considerably less expensive than most currently available automated perimeters. It could therefore make visual field examination available in situation where conventional methods are not possible.

REFERENCES

1. Harrington, D.O. (1981). The Visual Fields: A textbook and atlas of clinical perimetry. C.V. Mosby Comp.
2. Keltner, J.L. (1983). Screening for Visual Field Abnormalities with Automated Perimetry. Surv. Ophthamol., 28 (3), 175–182.
3. Schulzer, M., Mikelberg, F.S. (1987). A study of the value of the central and peripheral visual isoptres in assessing visual field progression in the presence of paracentral scotoma measurements. Br. Journ. Ophthalmol., 71, 422–427.
4. Weber, H., Dobek, K. (1986). What is the most suitable grid for computer perimetry in glaucoma patients. Ophthamol., 192, 88–96.
5. Accornero, N. (1984). Computerised video screen perimetry. Arch. Ophthamol., 102, 40–41.
6. Frisen, L. (1986). A computer graphics visual screener using high pass spatial frequency resolution targets and mulitple feedback devices. Doc. Ophthamol. Proc. Series 49, 441–446.
7. Fausset, T.M. (1986). A rapid technique for kinetic visual field determination in young children and adults with central retinal lesions. Doc. Ophthamol. Proc. Series 49, 495, 501.

I claim:

1. An oculoperimetric device for use in measuring the field of vision of a patient, which comprises
   an extended area visual target having a plurality of discrete localised target elements disposed adjacent a reference target element at a plurality of different angular and radial positions relative to the reference target;
   means for moving the visual target in a two-dimensional plane so as to keep the patient's attention fixed on the moving reference target element;
   follower means movable by the patient to follow the movement of the reference target element;
   localised target elements being visible or invisible to the patient, and each target element appearing visibly at least once during a test sequence;
   monitoring means operable by the patient dependent on whether or not he sees the appearance of each individual target element as it becomes visible; and
   recording means for recording whether or not each target element is seen by the patient, such as to provide a map of the patient's effective field of vision.

2. A device according to claim 1 wherein the target elements are spaced apart along lines extending radially from the reference target, the lines being equally angularly spaced.

3. A device according to claim 1 wherein at least one parameter of the target elements selected from size, colour and duration of appearance can be varied to suit individual patient requirements.

4. A device according to claim 1 wherein, if the appearance of any particular target element is not seen by the patient, then that target element is arranged to appear again more prominently at least once more.

5. A device according to claim 1 wherein the means for moving the visual target do so in a substantially random manner.

6. A device according to claim 1 wherein the reference target is a spot and the follower means is a cursor having a shape selected from circular, rectangular, square and pyramidal.

7. A device according to claim 1 wherein the speed of movement of the visual target can be varied so as to make successful operation of the follower means more 8. A device according to claim 1 in the form of a programmed computer, the reference target and individual target elements appearing on a computer screen, the follower means being a cursor operable by a mouse, and the results of the monitoring means being recorded and stored in the form of a map of the patient's effective field of vision.

9. A device according to claim 1 which further comprises means to keep the patient's eye at a fixed distance from the extended area visual target throughout the measurements.

* * * * *